United States Patent [19]

Warden et al.

[11] Patent Number: 5,081,662
[45] Date of Patent: Jan. 14, 1992

[54] MOBILE X-RAY APPARATUS

[75] Inventors: Hans-Erik Warden, Upplands Vaesby; Kent-Lennart Westergren, Jaerfaella, both of Sweden

[73] Assignee: Siemens Aktiengesellschaft, Berlin and Munich, Fed. Rep. of Germany

[21] Appl. No.: 544,313

[22] Filed: Jun. 27, 1990

[30] Foreign Application Priority Data

Jun. 28, 1989 [SE] Sweden .............................. 89023329

[51] Int. Cl.⁵ .............................................. H05G 1/02
[52] U.S. Cl. .................................... 378/198; 378/193; 378/196
[58] Field of Search ............... 378/193, 196, 198, 197, 378/195; 248/129, 667; 254/421

[56] References Cited

U.S. PATENT DOCUMENTS

| | | | |
|---|---|---|---|
| 1,239,145 | 9/1917 | Wantz | 378/197 |
| 3,790,805 | 2/1974 | Foderaro | 378/197 |
| 3,801,798 | 4/1974 | Götzl et al. | 378/198 |
| 3,918,682 | 11/1975 | Des palmes | 254/421 |
| 4,223,230 | 9/1980 | Wearve et al. | 378/197 |
| 4,326,131 | 4/1982 | Waerve | 378/197 |

Primary Examiner—Janice A. Howell
Assistant Examiner—Don Wong
Attorney, Agent, or Firm—Hill, Van Santen, Steadman & Simpson

[57] ABSTRACT

A mobile x-ray apparatus has an x-ray tube secured to a carriage via an arm mechanism, whereby the x-ray tube is adjustable both vertically and horizontally, and is provided with wheels for movement along a floor, and having a support which may be lowered to a floor to support the x-ray apparatus. Such a support, in its lowered position, supports the x-ray apparatus such that the x-ray apparatus is rotatable about the support, thereby improving the ease with which the x-ray tube may be positioned.

9 Claims, 3 Drawing Sheets

MOBILE X-RAY APPARATUS

BACKGROUND OF THE INVENTION

1. Field of the Invention

The present invention relates to a mobile x-ray apparatus of the type suitable for obtaining x-ray images.

2. Description of the Prior Art

A mobile x-ray apparatus having an x-ray tube, adjustable in both a vertical and a horizontal direction, allows for the collection of x-ray images without physical displacement of a patient. In such a mobile x-ray apparatus, as disclosed by the Siemens Brochure "Mobilett II", the arm mechanism supporting the x-ray tube has a mobile arm, pivotably connected to a stationary arm, and thereby attached to a support carriage. A boom, providing support for a vertical displacement, is disposed between the carriage and the stationary arm. The carriage is provided with wheels for movement along a floor.

A mobile x-ray apparatus is disclosed in U.S. Pat. No. 3,790,805, in which an x-ray tube is secured to a horizontal telescoping arm. The horizontal telescoping arm is attached to a vertical column, and rotatable about its axis. The vertical column is further connected to the carriage. Such an x-ray apparatus requires a large supporting surface to prevent the x-ray apparatus from falling to the floor upon adjustment of the telescoping arm, as the center of gravity of the x-ray apparatus is considerably displaced by movement of the telescoping arm. Such a large supporting surface makes it difficult to maneuver around a patient's bed.

SUMMARY OF THE INVENTION

It is an object of the present invention to further improve the initially recited mobile x-ray apparatus by providing a support, above which the x-ray apparatus may pivot, such that the wheels of the x-ray apparatus lift off the floor, allowing for a friction-free rotation of the x-ray apparatus relative to the floor.

It is a further object of the present invention to provide a support which unloads the wheels, leaving them in contact with the floor, such that rotation of the x-ray apparatus about the support is guided by the wheels.

The above objects are achieved in accordance with the principles of the present invention in a support which includes a drive mechanism for height adjustment. The support has a supporting plate, attached at one end to a bipartite articulated arm, and at an other end, rotatably connected to a carriage. The supporting plate may be height-adjusted by adjustment of the bipartite articulated arm via the drive mechanism. The supporting plate is connected to a shaft, secured by a spherical bearing, which in turn is attached to a bipartite articulated arm.

Thus, the supporting plate is self-adjusting to an uneven floor.

A further embodiment requires the supporting plate to be resiliently seated at the support, resulting in a uniform weight distribution. Such a support improves the efficiency with which portable x-ray images may be obtained.

DESCRIPTION OF THE PREFERRED EMBODIMENTS

Figure 1:
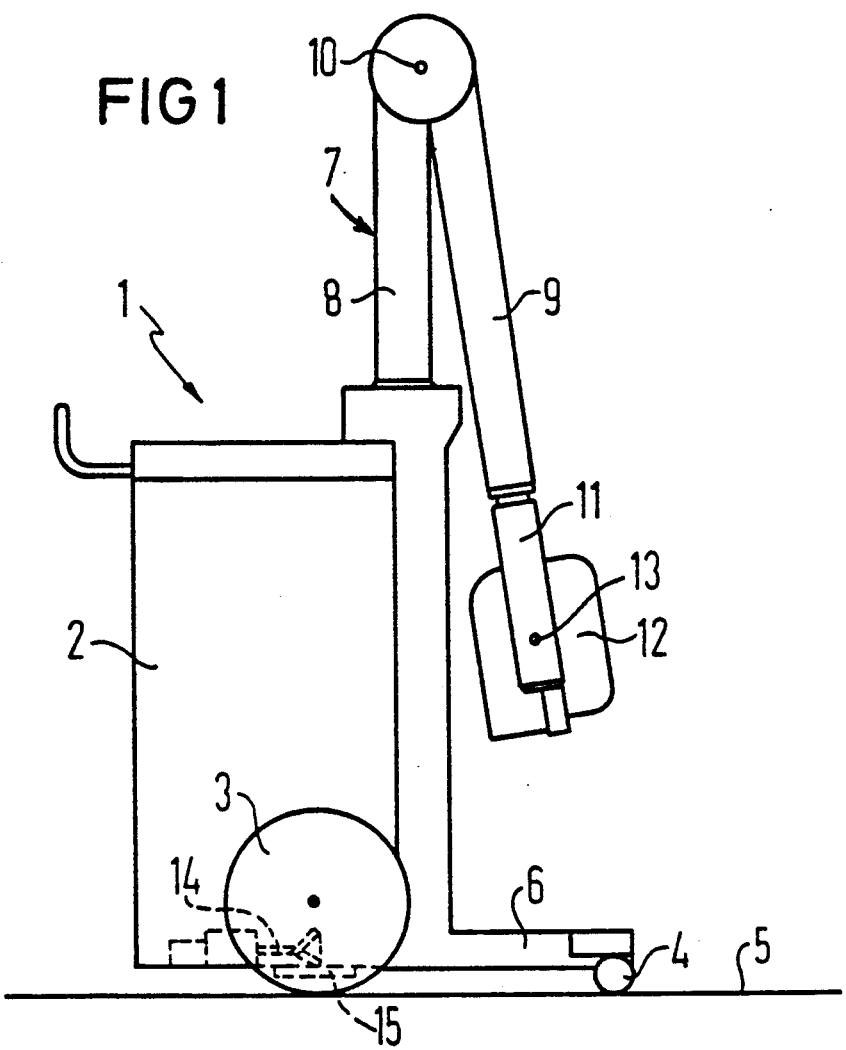
FIG. 1 is a side view of a mobile x-ray apparatus having a support in accordance with the principles of the present invention.

FIG. 1 is a mobile x-ray apparatus 1 consisting of a carriage 2 having two running wheels 3 and two steering wheels 4, which may be moved along a floor 5. The steering wheels 4 are secured by a boom 6, which is disposed between the carriage 2 and a stationary arm 8. The x-ray tube 12 is supported by a double arm 7, where the stationary arm 8 is secured to the upper side of the carriage 2 in a vertical position, and a mobile arm 9 is pivotably connected to the stationary arm 8 via an axis 10. A mount 11 is disposed between the mobile arm 9 and the x-ray tube 12, and is rotatable about the axis 13. FIG. 1 shows the x-ray tube 12 in a standby position. The boom 6 serves as a support for vertical displacement of the x-ray tube. The mobile arm 9 may be pivoted about the axis 10 into a desired position. The support 14 is disposed between the running wheels 3. A further description of the support 14 shall be set forth in connection with FIGS. 3 and 4.

Figure 2:
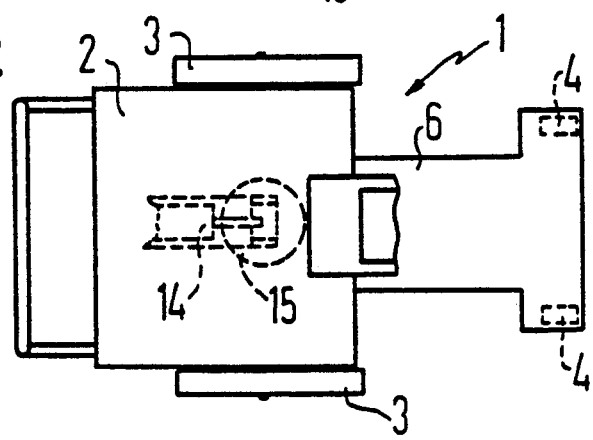
FIG. 2 is a bottom plan view of the mobile x-ray apparatus containing a support in accordance with the principles of the present invention.

FIG. 2 displays a support 14 disposed between the running wheels 3.

Figure 3:
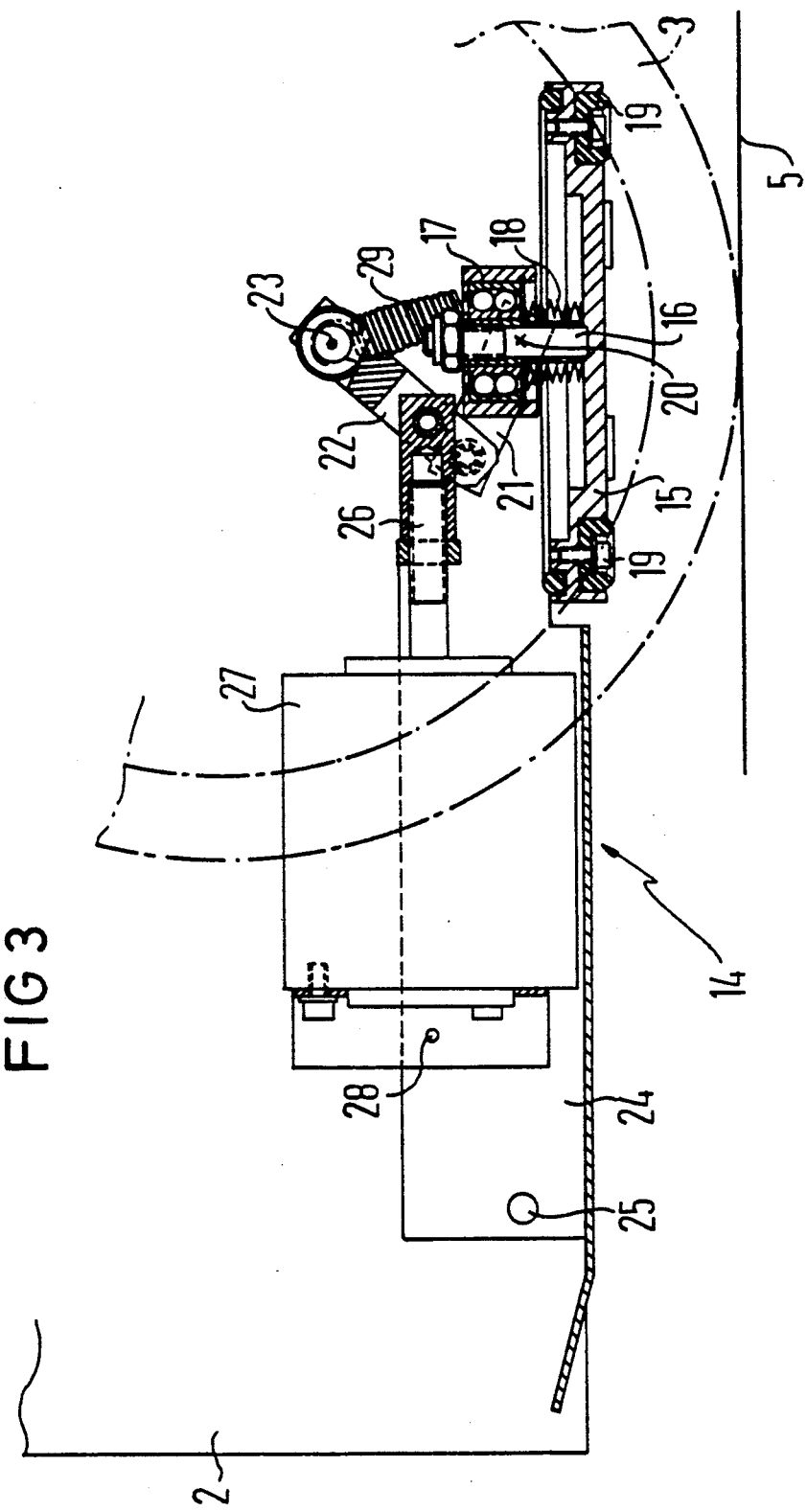
FIG. 3 is a sectional view demonstrating a support in an upward position in accordance with the principles of the present invention.

FIG. 3 shows a support 14 provided with a supporting plate 15 and a bearing pin 16, which is pivotably seated into a spherical bearing 17. The supporting plate 15 is resiliently seated with a spring 18, arranged around the bearing pin 16, and disposed between the supporting plate 15 and the spherical bearing 17. The supporting plate 15 is also provided with a plurality of rubber plugs 19. The bearing 17 is pivotable about an axis 20, and connected via the axis 20 to the end 21 of a bipartite articulated arm 21, 22. The end 22 of the bipartite articulated arm 21, 22 is rotatable about an axis 23, which is secured to the carriage 2. The axis 20 is also attached to a console 24, which is rotatably connected to the carriage 2 via an axis 25. A drive rod 26 is driven by an electromagnet 27, which is rotatably secured to the console 24 via an axis 28. The axis 28 is secured to the arm 22 of the bipartite articulated arm 21, 22.

Figure 4:
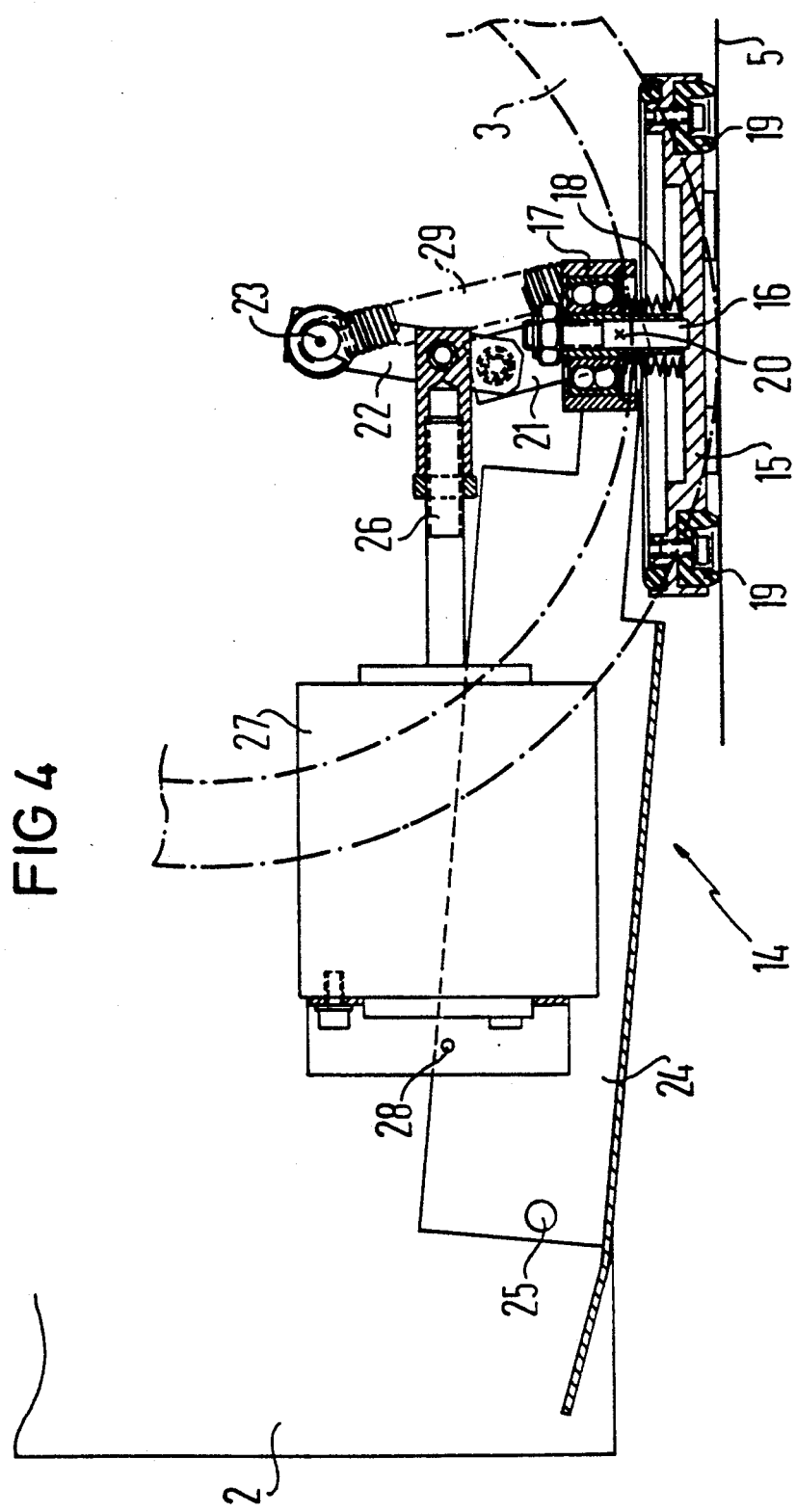
FIG. 4 is a sectional view of a support in a lowered position in accordance with the principles of the present invention.

FIG. 4 shows the support 14 in a lowered position. Support 14 is lowered by activating the electromagnet 27, which displaces the drive rod 26, and presses against the bipartite articulated arm 21, 22, thereby deflecting the articulated arm 21, 22. Simultaneously, the console 24 rotates about its axis 25. When the supporting plate 15 is in a lowered position, it is disposed between the running wheels 3 as shown in FIG. 2. The weight of the x-ray apparatus 1 may be shifted from the running wheels 3 to the supporting plate 15 when the spherical bearing 17 and the spring 18 are engaged. In this configuration, the running wheels 3 will serve as floor support.

Activating the electromagnet 27 causes the tension spring 29, to hinge the bipartite articulated arm 21, 22, thus forcing the drive rod 26 into the electromagnet 27, returning the supporting plate 15 to a standby position.

The support 14 may also be driven by an electric motor having a spindle, which would replace the electromagnet 27 and the drive rod 26. In an embodiment in which the support 14 lifts the x-ray apparatus 1 such that the wheels 3, 4 are lifted from the floor, it is not necessary for the supporting plate 15 to be disposed centrally between the running wheels 3.

Although other modifications and changes may be suggested by those skilled in the art, it is the intention of the inventors to embody within the patent warranted hereon all changes and modifications as reasonably and properly come within the scope of their contribution to the art.

We claim:

1. A mobile x-ray apparatus comprising:
   an x-ray tube;
   a carriage, having wheels for movement along a floor;
   an arm mechanism, connecting said x-ray tube at one side of said carriage; and
   selectively actuatable support means mounted on said carriage, maintained spaced from the floor during movement of the carriage along the floor and upon actuation projecting from beneath said carriage, for solely supporting the entirety of said carriage and permitting free rotation of said carriage around said selectively actuatable support means, including means for shifting the weight of said mobile x-ray apparatus to said selectively actuatable support means, thereby unloading said wheels, such that said wheels serve as floor supports in rotation of said x-ray apparatus about said selectively actuatable support means.

2. A mobile x-ray apparatus as claimed in claim 1, wherein said arm mechanism includes means for selectively vertically and horizontally adjusting said x-ray tube.

3. A mobile x-ray apparatus as claimed in claim 1, wherein said selectively actuatable support means includes a drive mechanism for adjusting the height of said selectively actuatable support means.

4. A mobile x-ray apparatus as claimed in claim 1, wherein said drive mechanism includes an electromagnet having a drive rod.

5. A mobile x-ray apparatus as claimed in claim 3, wherein said drive mechanism includes an electronic motor having a threaded rod.

6. A mobile x-ray apparatus as claimed in claim 1, wherein said selectively actuatable support means includes a supporting plate attached to one end of a bipartite articulated arm, said bipartite articulated arm having hinged ends foldable and spreadable by a drive mechanism to adjust the height of said selectively actuatable support means.

7. A mobile x-ray apparatus as claimed in claim 1, wherein said carriage is selectively stored in a standby position spaced from the floor, and wherein said wheels further include at least two running wheels and at least two steering wheels connected to said carriage, with a supporting plate disposed substantially between said running wheels when said carriage is in a lower position than said standby position.

8. A mobile x-ray apparatus as claimed in claim 1, wherein said selectively actuatable support means further includes a drive mechanism connected to a mechanical assembly including a support plate connected to a shaft, said shaft being secured at one end by a spherical bearing and said bearing being attached to a bipartite articulated arm, said bipartite articulated arm being secured to said drive mechanism for selectively positioning said carriage with respect to the floor.

9. A mobile x-ray apparatus comprising:
   an x-ray tube;
   a carriage, having wheels for movement along a floor;
   an arm mechanism, connecting said x-ray rube at one side of said carriage; and
   selectively actuatable support means mounted on said carriage, maintained spaced from the floor during movement of the carriage along the floor and upon actuation projecting from beneath said carriage, for solely supporting the entirety of said carriage and permitting free rotation of said carriage around said selectively actuatable support means, said selectively actuatable support means including a drive mechanism connected to a mechanical assembly including a support plate connected to a shaft, said shaft being secured at one end by a spherical bearing and said bearing being attached to a bipartite articulated arm, said bipartite articulated arm being secured to said drive mechanism for selectively positioning said carriage with respect to the floor.

* * * * *